United States Patent
Wan

(10) Patent No.: US 9,404,910 B2
(45) Date of Patent: Aug. 2, 2016

(54) BODY FLUID TESTING APPARATUS WITH TESTING AND STORING FUNCTIONS

(75) Inventor: John Wan, San Marino, CA (US)

(73) Assignee: W.H.P.M. BIORESEARCH & TECHNOLOGY CO., LTD., Beijing (CN)

( * ) Notice: Subject to any disclaimer, the term of this patent is extended or adjusted under 35 U.S.C. 154(b) by 545 days.

(21) Appl. No.: 13/884,809

(22) PCT Filed: Nov. 12, 2010

(86) PCT No.: PCT/CN2010/001814
§ 371 (c)(1),
(2), (4) Date: Jul. 24, 2013

(87) PCT Pub. No.: WO2012/061957
PCT Pub. Date: May 18, 2012

(65) Prior Publication Data
US 2014/0150539 A1 Jun. 5, 2014

(51) Int. Cl.
*G01N 1/00* (2006.01)
*G01N 33/487* (2006.01)
*A61B 10/00* (2006.01)
*B01L 3/00* (2006.01)

(52) U.S. Cl.
CPC ........ *G01N 33/4875* (2013.01); *A61B 10/0045* (2013.01); *A61B 10/0096* (2013.01); *B01L 3/5029* (2013.01); *B01L 2200/0684* (2013.01); *B01L 2300/046* (2013.01); *B01L 2300/0663* (2013.01)

(58) Field of Classification Search
CPC ....... G01N 1/10; G01N 1/28; B01L 3/502715

USPC ....................................................... 73/64.56
See application file for complete search history.

(56) References Cited

U.S. PATENT DOCUMENTS

| 7,029,627 B2 | 4/2006 | Alley | |
| 7,090,803 B1* | 8/2006 | Gould | B01L 3/5023 422/413 |
| 7,270,959 B2 | 9/2007 | Hudak | |
| 2003/0049848 A1* | 3/2003 | Gebrian | B01L 99/00 436/55 |

(Continued)

FOREIGN PATENT DOCUMENTS

CN 201251578 Y 6/2009

OTHER PUBLICATIONS

International Search Report for International Application No. PCT/CN2010/001814, mailed Aug. 18, 2011, with English translation.

*Primary Examiner* — Hezron E Williams
*Assistant Examiner* — Rodney T Frank
(74) *Attorney, Agent, or Firm* — Scully Scott Murphy & Presser

(57) ABSTRACT

A body fluid testing apparatus with testing and storing functions is provided, which comprises a body, a cover, at least two body fluid collectors and a testing element. The body comprises a fluid storing chamber, a testing chamber and a partition wall. The fluid storing chamber and the testing chamber are divided by the partition wall. The body is covered by the cover with at least two through-holes through which the body fluid collectors respectively enter into the fluid storing chamber and the testing chamber. The testing element is inserted into the testing chamber. Pollution is avoided, which results from that the body fluid in the testing chamber cannot flow back into the fluid storing chamber.

19 Claims, 8 Drawing Sheets

(56) References Cited

U.S. PATENT DOCUMENTS

| | | | |
|---|---|---|---|
| 2003/0190259 A1* | 10/2003 | Alley | A61B 10/0051 422/411 |
| 2005/0112547 A1* | 5/2005 | Youngkin | C12Q 1/04 435/4 |
| 2005/0232813 A1* | 10/2005 | Karmali | A61B 5/1411 422/410 |
| 2006/0029517 A1* | 2/2006 | Hartselle | A61B 10/0096 422/400 |
| 2007/0025886 A1* | 2/2007 | Yong | A61B 10/0045 422/400 |
| 2007/0275475 A1* | 11/2007 | Liang | B01L 3/502 436/165 |
| 2008/0112847 A1* | 5/2008 | Chen | G01N 21/03 422/400 |
| 2008/0118397 A1* | 5/2008 | Slowey | A61B 10/0051 422/400 |
| 2009/0004058 A1* | 1/2009 | Liang | A61B 10/0096 422/68.1 |
| 2009/0306543 A1* | 12/2009 | Slowey | A61B 10/0051 600/576 |
| 2010/0043574 A1* | 2/2010 | Katsumata | B01L 3/50825 73/864 |
| 2010/0288060 A1* | 11/2010 | Ronsick | G01N 35/0099 73/864.63 |
| 2012/0306628 A1* | 12/2012 | Singhal | A61B 5/1411 340/10.6 |

\* cited by examiner

BODY FLUID TESTING APPARATUS WITH TESTING AND STORING FUNCTIONS

This is the U.S. national stage of application No. PCT/CN2010/001814, filed on 12 Nov. 2010.

TECHNICAL FIELD

The present disclosure generally relates to a medical apparatus, and particularly to a body fluid testing apparatus with testing and storing functions.

BACKGROUND ART

Body fluid testing apparatus currently have been commercially available, and have been reported in several patent documents. Such apparatuses can be used to test for drugs, glucose and parasite mixtures, and alternatives for antigen and antibody in body fluid.

U.S. Pat. No. 7,270,959 discloses a specimen collection container mainly for testing of urine, which comprises: a chamber for collecting a specimen; a reservoir; and a valve interposed between the chamber and the reservoir. The valve body of the valve has a compartment for transporting a portion of specimen from the chamber to the reservoir. Such specimen collection container is merely suitable for testing urine samples, but is not suitable for testing body fluid samples such as saliva with a small amount of collection.

U.S. Pat. No. 7,507,373 discloses an assay device mainly for testing urine, which comprises: a transparent container for retaining a liquid sample to be tested; a testing member in said container; and test strips in said testing member.

Chinese Patent Application No. 201251578 discloses an apparatus for body fluid collections and tests. All the apparatuses as described above are merely suitable for the preliminary screening of body fluid samples, but have no storing function for the samples required to be screened twice or more times.

Thus, there is a demand for a simple apparatus for body fluid tests, to overcome the problem that the conventional apparatuses for body fluid tests can not implement both the preliminary screening and the secondary screening of the volatile body fluids such as saliva.

SUMMARY OF THE INVENTION

An object of the present disclosure is to provide a body fluid testing apparatus with testing and storing functions. The body fluid testing apparatus can carry out both the preliminary screening and the secondary screening, and can even be sent far away for secondary screening, while the samples to be tested can be still well preserved.

In one aspect, the present disclosure provides an body fluid testing apparatus with testing and storing functions, comprising: a body, a cover, at least two body fluid collectors and a testing element, wherein the body comprises a fluid storing chamber, a testing chamber and a partition wall, and the fluid storing chamber and the testing chamber are divided by the partition wall; the cover is disposed on and covers the body and is provided with at least two through-holes, and the at least two body fluid collectors capable of entering into the fluid storing chamber and the testing chamber through the at least two through-holes respectively; the testing element is capable of being inserted into the testing chamber and positioned against the inner wall of the testing chamber, and comprises a main part with several channels for containing test strips and an inserting end extending downward from two edges of the main part.

Preferably, the fluid storing chamber comprises a body fluid squeezing region, a body fluid flow channel and a body fluid reservoir, and the body fluid squeezing region is communicated with the body fluid reservoir though the body fluid flow channel.

Preferably, the body fluid reservoir partly surrounds the periphery of the body fluid squeezing region, and the body fluid squeezing region comprises a squeezing plate and a wall plate extending upward from the edge of the squeezing plate.

Preferably, the squeezing plate in the body fluid squeezing region is positioned higher than the bottom plate of the body fluid reservoir, or positioned at the same level as the bottom plate of the body fluid reservoir.

Preferably, the wall plate is provided with at least one opening as the body fluid flow channel, and a lower part of the body fluid collector capable of entering into the space defined by the wall plate and the squeezing plate to avoid a horizontal displacement during being squeezed.

Preferably, the fluid storing chamber further comprises a partition plate, a top opening of the body fluid squeezing region is located on the partition plate, and the body fluid reservoir is located below the partition plate, the body fluid squeezing region is defined by a squeezing plate and a wall plate extending upward from the edge of the squeezing plate, and the lower part of the body fluid collector enters into the space defined by the wall plate and the squeezing plate, to avoid a horizontal displacement during being squeezed.

Preferably, the squeezing plate is provided with at least one opening as the body fluid channel.

Preferably, the testing chamber comprises a body fluid squeezing region, a body fluid flow channel and a slot, the slot is used to contain the inserting end of the testing element, and the body fluid flow channel communicates the body fluid squeezing region with the slot.

Preferably, the body fluid squeezing region is defined by a squeezing plate and a wall plate extending upward from the edge of the squeezing plate, and a lower part of the body fluid collector enters into the space defined by the wall plate and the squeezing plate, to avoid a horizontal displacement during being squeezed.

Preferably, the body fluid flow channel is configured to be concaved from the surface of the squeezing plate and communicated with the slot, and the bottom of the slot is located at a position lower than that of the squeezing plate.

Preferably, the wall plate is provided with at least one opening as the body fluid flow channel, and the bottom of the slot is positioned at a same level as the squeezing plate.

Preferably, an opening is disposed at the side wall of the fluid storing chamber or the upper surface of the cover, which is sealed with a sealing plug provided on a covering plate of the fluid storing chamber.

Preferably, the body fluid collector comprises a handle, a sampling end and a connecting bar connecting the handle with the sampling end.

Preferably, a coupling member is disposed in each of the through-holes of the cover, and the handle is provided with an adapting member matching to the coupling member.

Preferably, the coupling member is screw thread or fastener.

Preferably, the sampling end is made from absorbent material.

Preferably, a press plate is further provided on the lower end of the connecting bar, and the sampling end is connected to the bottom of the press plate.

Preferably, the body fluid testing apparatus is a saliva testing apparatus.

Preferably, the front surface and the back surface of the body of the body fluid testing apparatus are parallel to each other.

The present disclosure may have the following beneficial effects: since the body fluid testing apparatus according to the present disclosure has both the testing chamber and the fluid storing chamber, it can implement accordingly both the preliminary screening and the secondary exact screening for the samples. Further, according to the present disclosure, the testing chamber and the fluid storing chamber are not communicated with each other, and thereby it can be assured that the samples to be tested are not polluted during the rescreening and not affected by the preliminary screening.

Since the fluid storing chamber of the apparatus according to the present disclosure has an opening which can be sealed, the samples can be taken out through the opening for being tested.

Additionally, in view of high volatility and small sampling amount of the body fluid samples, especially for saliva samples, the collector of the apparatus according to the present disclosure is disposed in the fluid storing chamber with being completely squeezed, such that it can prevent the body fluid samples stored in the fluid storing chamber being reabsorbed by the collector due to the incomplete squeezing of the collector.

In the condition that the amount of the body fluid sample in the fluid storing chamber is small during the secondary screening, diluent can be added into the fluid storing chamber through the opening which can be sealed, such that the coagulation of saliva in the collector and the storing chamber can be dissolved, allowing the secondary screening to be achieved.

Further, according to the present disclosure, a body fluid reservoir containing saliva is disposed on the bottom of the fluid storing chamber, such that the body fluid or saliva collected can be gathered in the reservoir, which facilitates the sampling of saliva by the examiner during the secondary screening.

Further, since the two surfaces opposing to each other of the body of the body fluid testing apparatus according to the present disclosure are flat surfaces, the body fluid testing apparatus can be copied with a duplicator, and information about the subjects can also be recorded on said two opposing surfaces.

The foregoing and other features and advantages of the disclosure will be apparent to those skilled in the art in view of the following detailed description, taken in conjunction with the accompanying drawings.

DETAILED DESCRIPTION

The First Embodiment

Figure 1:
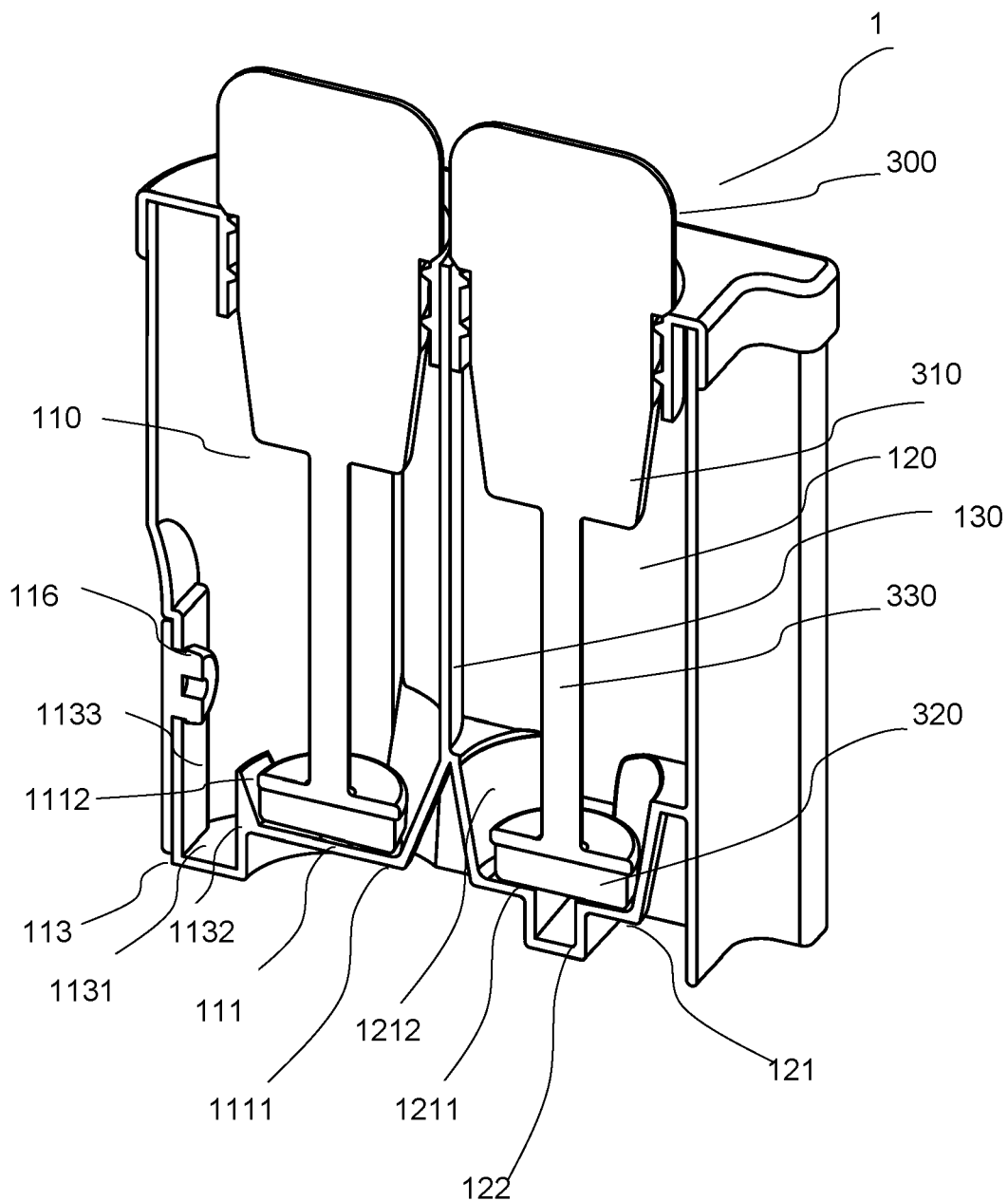
FIG. 1 illustrates a perspective cross-sectional view of the body fluid testing apparatus according to the first embodiment of the present disclosure.
Figure 2:
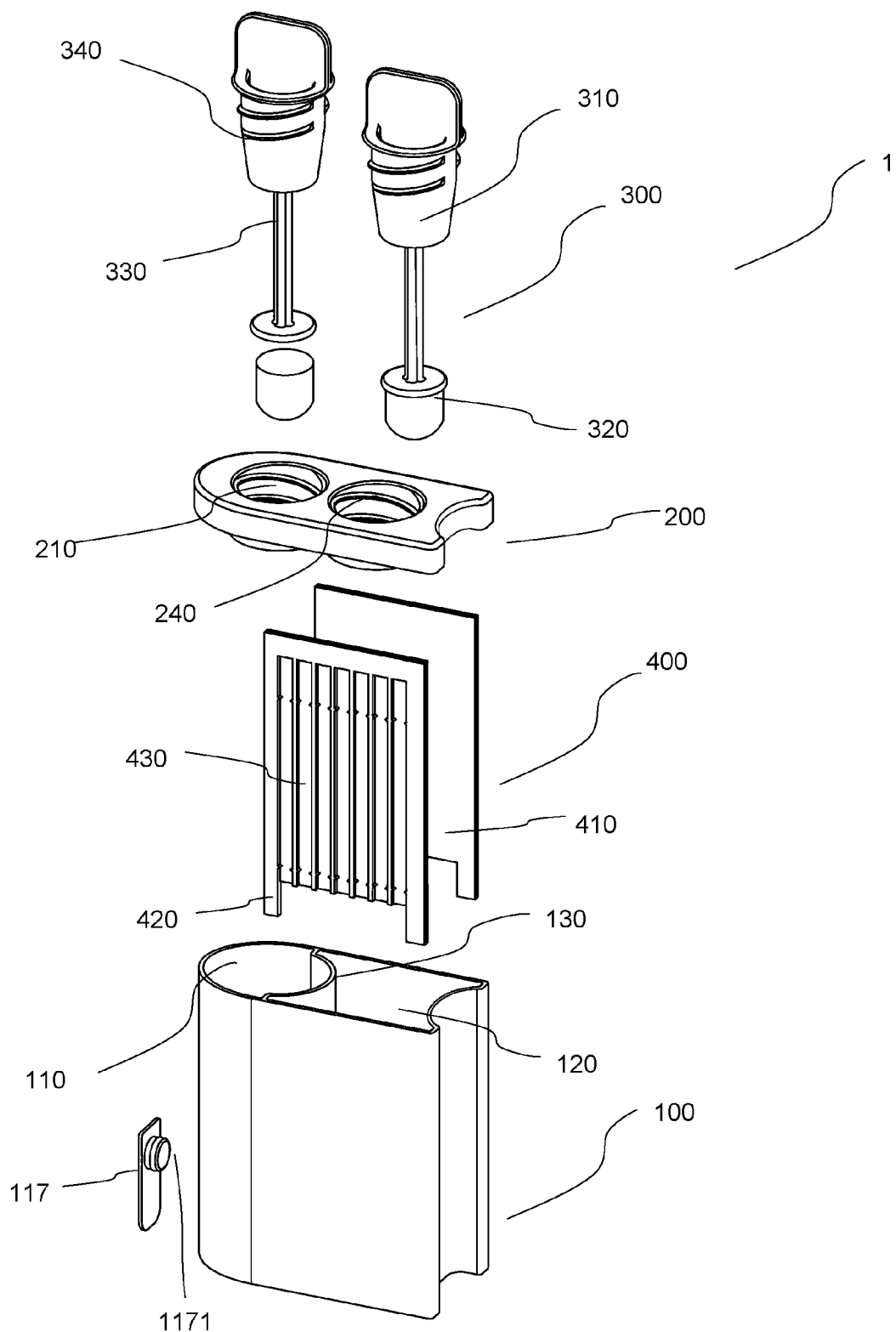
FIG. 2 illustrates a perspective exploded view of the body fluid testing apparatus according to the first embodiment of the present disclosure.
Figure 3:
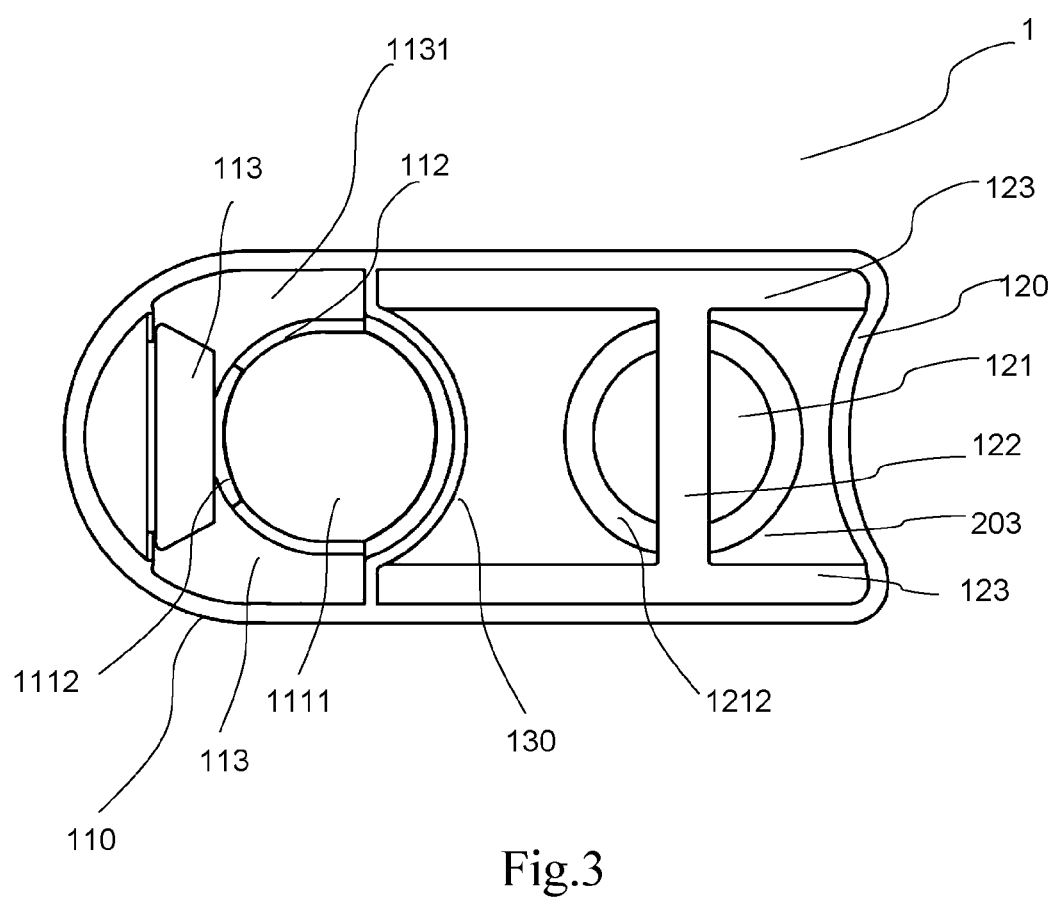
FIG. 3 illustrates a top view of the body fluid testing apparatus according to the first embodiment of the present disclosure.

As shown in FIGS. 1-3, the body fluid testing apparatus 1 comprises a body 100, a cover 200, a body fluid collector 300 and a testing element 400. The body 100 comprises a fluid storing chamber 110, a testing chamber 120 and a partition wall 130 for dividing the fluid storing chamber 110 from testing chamber 120. The cover 200 is disposed on and covers the body 100 and is provided with two through-holes 210 each having internal thread 240. The body fluid collector 300 comprises a handle 310, a sampling end 320, and a connecting bar 330 connecting the handle 310 with the sampling end 320. The handle 310 is provided with external thread 340 to engage with the internal thread 240. The sampling end 320 is made of absorbent material such as sponge. A press plate can be provided at the lower end of the connecting bar 330, and the sampling end 320 is connected to the bottom of the press plate, such that the press plate can assist to squeeze the sampling end. The testing elements 400 are disposed parallel to each other in the testing chamber 120, and are closely attached to two inner walls of the testing chamber 120. The testing element 400 comprises a main part 410 and an inserting end 420. The main part 410 is provided with several channels 440 for containing the test strips. The inserting end 420 extends downward from two ends of the main part 410. In this embodiment, the testing elements 400 are two pieces of testing cards.

The internal structure of the body 100 will be described in detail below.

The bottom of the fluid storing chamber 110 is defined by a body fluid squeezing region 111, a body fluid flow channel 112 and a body fluid reservoir 113. The body fluid reservoir 113 partly surrounds the periphery of the body fluid squeezing region 111. The body fluid squeezing region 111 comprises a squeezing plate 1111 and a wall plate 1112 extending a certain distance upward from the edge of the squeezing plate 1111. A part of the wall plate 1112 extends upward until reaching and connecting with the partition wall 130. The body fluid reservoir 113 comprises a bottom plate 1131, an inner wall 1132 and an outer wall 1133. The squeezing plate 1111 of the body fluid squeezing region 111 is located at a position higher than that of the bottom plate 1131 of the body fluid reservoir 113. The inner edge of the bottom plate 1131 extends upward to form the inner wall 1132 connected with the squeezing plate 1111. The outer wall 1133 serves as the side wall of the fluid storing chamber 110 and the side wall of the body 100 as well. The wall plate 1112 of the body fluid squeezing region 111 is provided with two openings, which extend from the periphery of the wall plate 1112 to the squeezing plate 1111 and are communicated with the body fluid reservoir 113, serving as the body fluid flow channel 112.

The side wall of the fluid storing chamber 110 is provided with a through-hole 116, and the fluid storing chamber 110 is further provided with a covering plate 117 having a sealing plug 1171. The covering plate 117 is mounted on the side wall of the fluid storing chamber 110 via the sealing plug 1171 with the through-hole 116 being sealed by the sealing plug 1171.

The bottom of the testing chamber 120 is defined by a body fluid squeezing region 121, a body fluid flow channel 122 and a slot 123. The body fluid squeezing region 121 comprises a squeezing plate 1211 and a wall plate 1212 extending a certain distance upward from the edge of the squeezing plate 1211. A part of the wall plate 1212 extends upward until reaching and connecting with the partition wall 130, and a part extends upward until reaching and connecting with the side wall of the testing chamber 120. The slots 123 are provided on opposite sides of the wall plate 1212 to contain the inserting end 420 of the testing element 400, such that the testing element 400 is able to be disposed in the testing chamber 120. The body fluid flow channel 122 is configured to be concaved from the squeezing plate 1211 and communicated with the slot 123, wherein the top opening of the body fluid flow channel is located on squeezing plate 1211 and both ends of the body fluid flow channel are communicated with two slots 123. The bottom of the slot 123 is located at a position lower than that of the squeezing plate 1211.

The use of the body fluid testing apparatus will be explained below.

When in use, the body fluid collector 300 in the fluid storing chamber 110 and the body fluid collector 300 in the testing chamber 120 are taken out, respectively, and then put into mouth in turn. After sponges at the sampling ends 320 of the body fluid collectors become saturated, the handle 310 of one of the body fluid collectors 300 is held and screwed into the fluid storing chamber 110, such that the external thread 340 on the handle 310 is tightly engaged with the internal thread 240 on the fluid storing chamber 110. Under the condition of being tightly screwed, the sampling end 320 is tightly pressed against the squeezing plate 1111 in the fluid storing chamber 110, and the moving of the collector 300 is limited by the wall plate 1112 in the body fluid squeezing region 111 in right and left directions, such that the body fluid collector is sufficiently squeezed. Saliva in the body fluid squeezing region 111 flows into the body fluid reservoir 113 through the body fluid flow channel 112, such that the storing of saliva in the fluid storing chamber 110 is achieved. Since the external thread 340 on the body fluid collector is tightly engaged with the internal thread 240 on the fluid storing chamber, the pollution of saliva in the fluid storing chamber is avoided.

Similarly, the other body fluid collector 300 is subsequently screwed into the testing chamber 120, such that the sampling end 320 of the body fluid collector 300 is squeezed. The length from the top of the testing chamber 120 to squeezing plate 1211 is fit for disposing the squeezed body fluid collector 300. Under the condition of being tightly screwed, the sampling end 320 is tightly pressed against squeezing plate 1211 of the body fluid squeezing region 121 in the testing chamber 120, and the moving of the sampling end 320 is limited by the wall plate 1212 of the body fluid squeezing region 121 in right and left directions. Saliva in the body fluid squeezing region 121 flows downward into the slot 123 through the body fluid flow channel 122 and then runs upward along the test strip on the testing element 400 in the testing chamber 120. A mark will appear on the test strip according to the analyte contained in the saliva.

When the sample to be tested is required for rescreening, the body fluid collector will be sent to the rescreening institution. Then, the sealing plug 1171 on the side wall of the fluid storing chamber 110 is pulled out, and the untested saliva sample in the fluid storing chamber 110 can be taken out for re-screening by the user with a pipette via the through-hole 116, or the sample may be taken out with a pipette via the through-hole 210 after the body fluid collector is screwed off the fluid storing chamber 110.

The Second Embodiment

Figure 4:
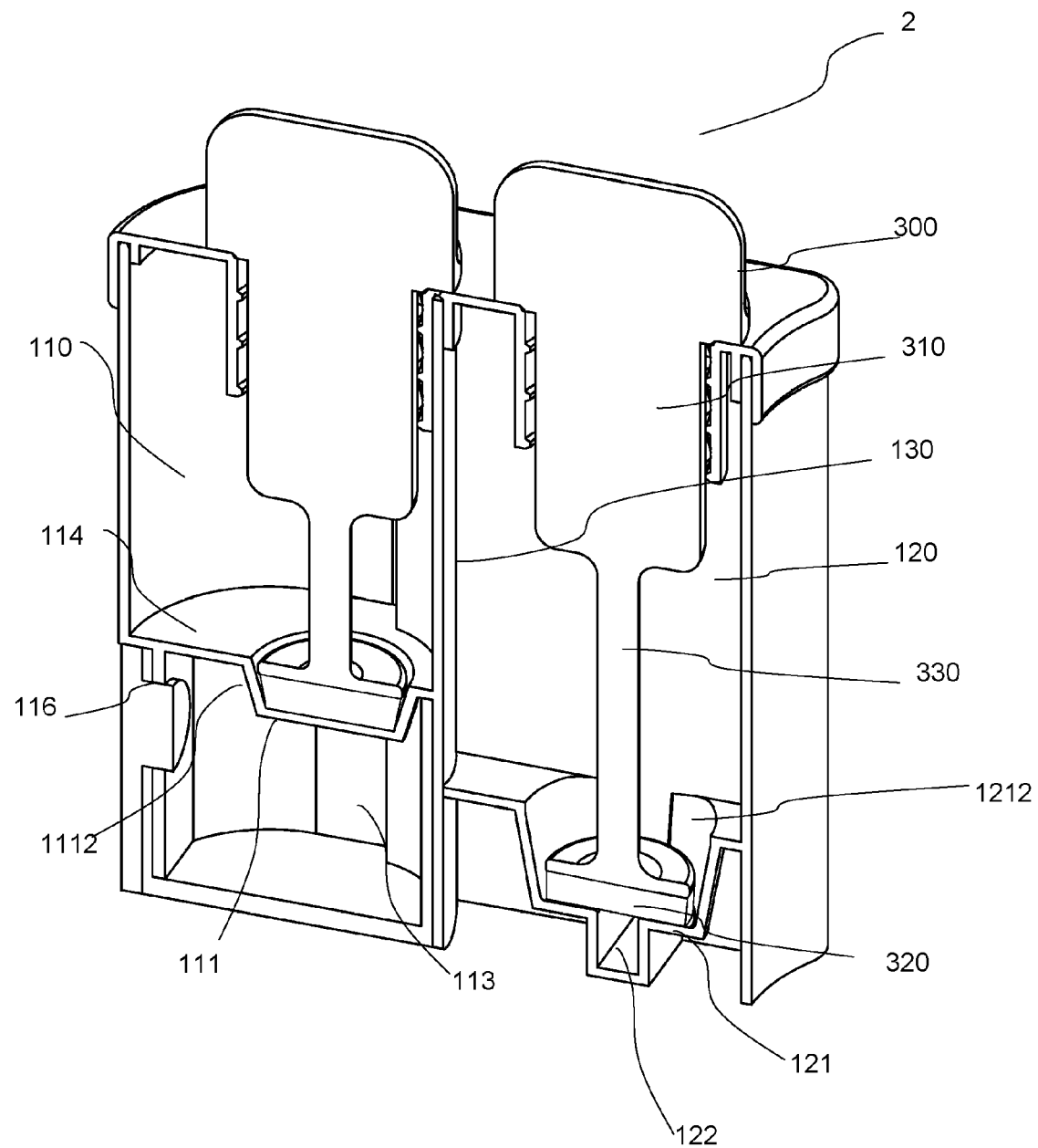
FIG. 4 illustrates a perspective cross-sectional view of the body fluid testing apparatus according to the second embodiment of the present disclosure.
Figure 5:
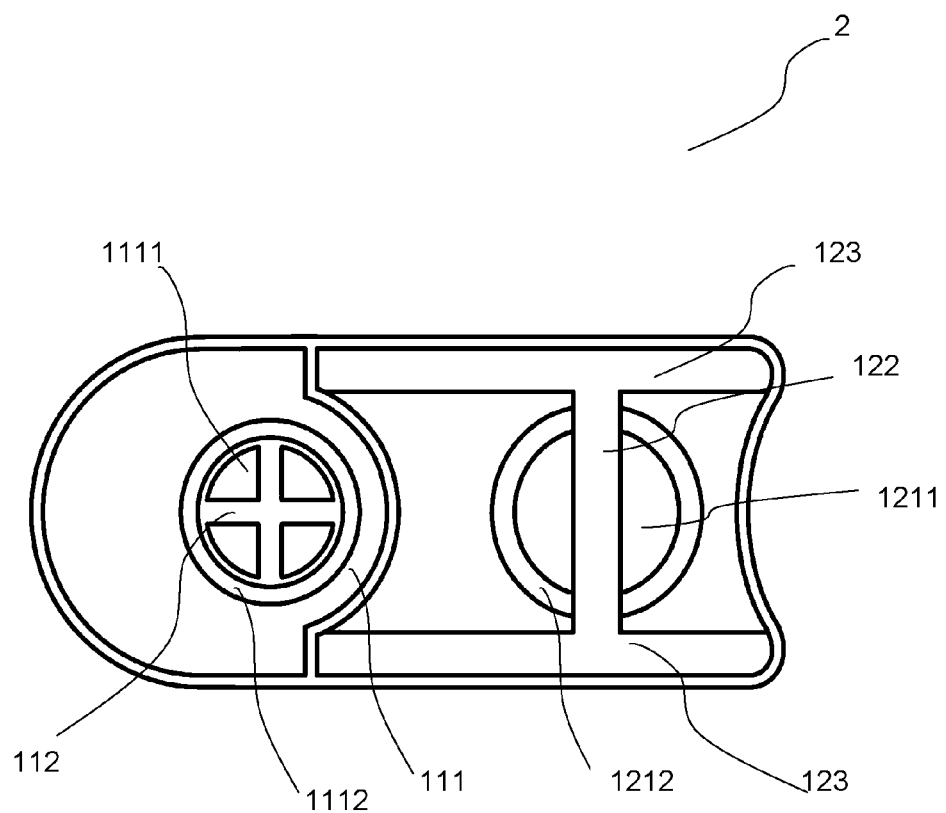
FIG. 5 illustrates a top view of the body fluid testing apparatus according to the second embodiment of the present disclosure.

The body fluid testing apparatus 2 as shown in FIGS. 4-5 is different from that in the first embodiment as described below.

The fluid storing chamber 110 is further provided with a partition plate 114 horizontally positioned in the fluid storing chamber 110, such that the fluid storing chamber 110 can be divided into two spaces in up and down directions; the partition plate 114 is provided with a body fluid squeezing region 111 and a body fluid flow channel 112, wherein the top opening of the body fluid squeezing region 111 is located on the partition plate 114, and a body fluid reservoir 113 is located in the fluid storing chamber 110 below the partition plate 114; a wall plate 1112 of the body fluid squeezing region 111 extends downward from an opening of the partition plate 114, and a squeezing plate is disposed in the space defined by the wall plate 1112.

As shown in FIG. 5, the squeezing plate 1111 in the body fluid squeezing region 111 is provided with two openings as the body fluid flow channel 112. When the handle 310 is tightly screwed, the sampling end 320 is tightly pressed against the squeezing plate 1111 in the fluid storing chamber, and the moving of the sampling end 320 is limited by the wall plate 1112 of the body fluid squeezing region 1111 in right and left directions, such that the sampling end 320 is sufficiently squeezed. Saliva in the body fluid squeezing region 111 flows into the body fluid reservoir 113 below through the body fluid flow channel 112.

In this embodiment, the fluid storing chamber 110 is divided into two spaces by the partition plate 114, and body fluid flow channel 112 is blocked by the sampling end 320 of the body fluid collector 300, and meanwhile, the sampling end 320 is unable to absorb body fluid in the body fluid reservoir 113 under the condition of being sufficiently squeezed, such that the body fluid reservoir 113 of the fluid storing chamber 110 is sealed. Since body fluid is not likely to contact with other elements in the fluid storing chamber due to swaying during the transport of the apparatus, the pollution of body fluid in the fluid storing chamber is avoided, and the loss of body fluid is also reduced.

The structure and the use of the testing chamber according to this embodiment are similar to those according to the first embodiment, and then will not be described herein in detail.

The Third Embodiment

Figure 6:
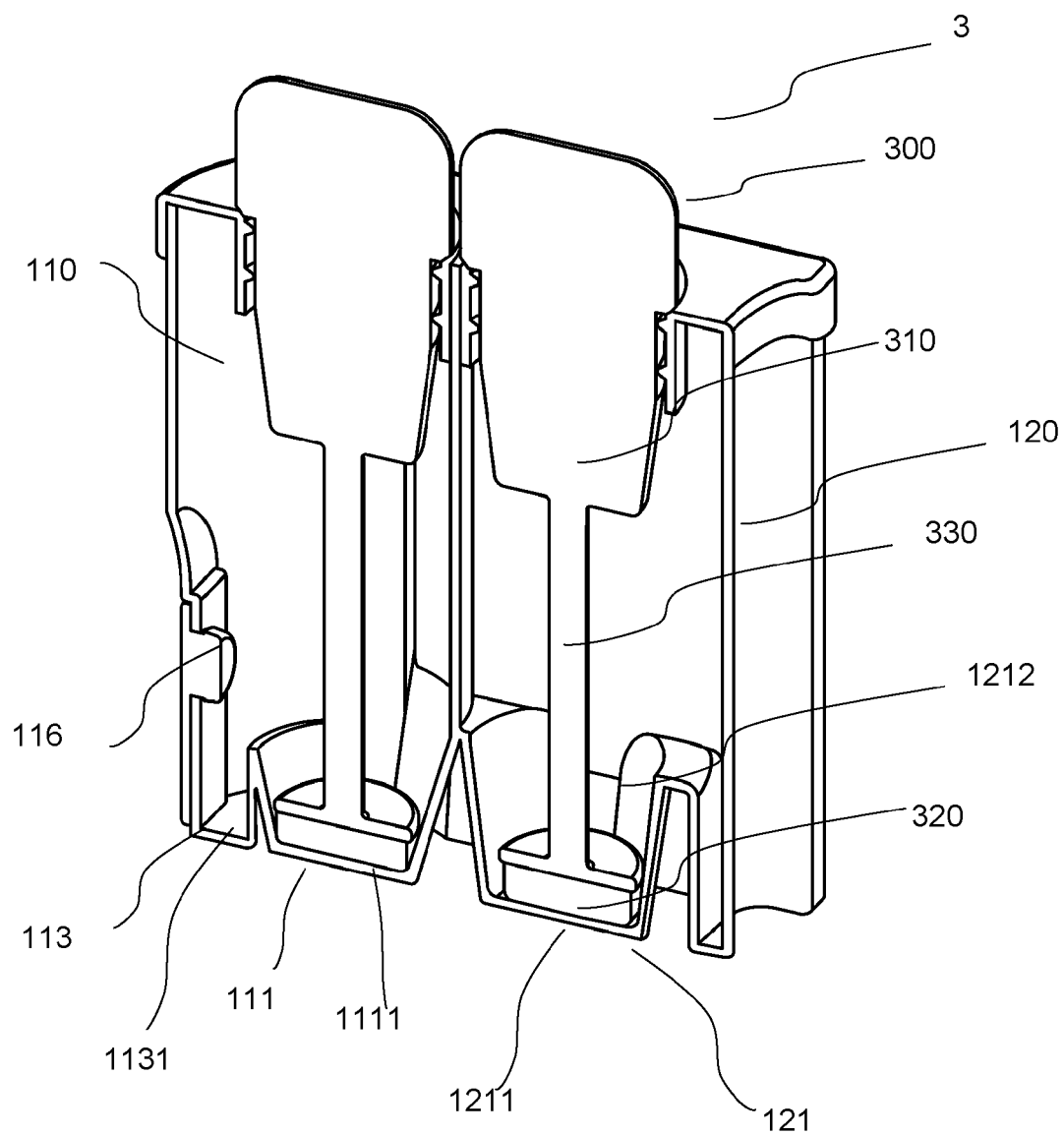
FIG. 6 illustrates a perspective cross-sectional view of the body fluid testing apparatus according to the third embodiment of the present disclosure.
Figure 7:
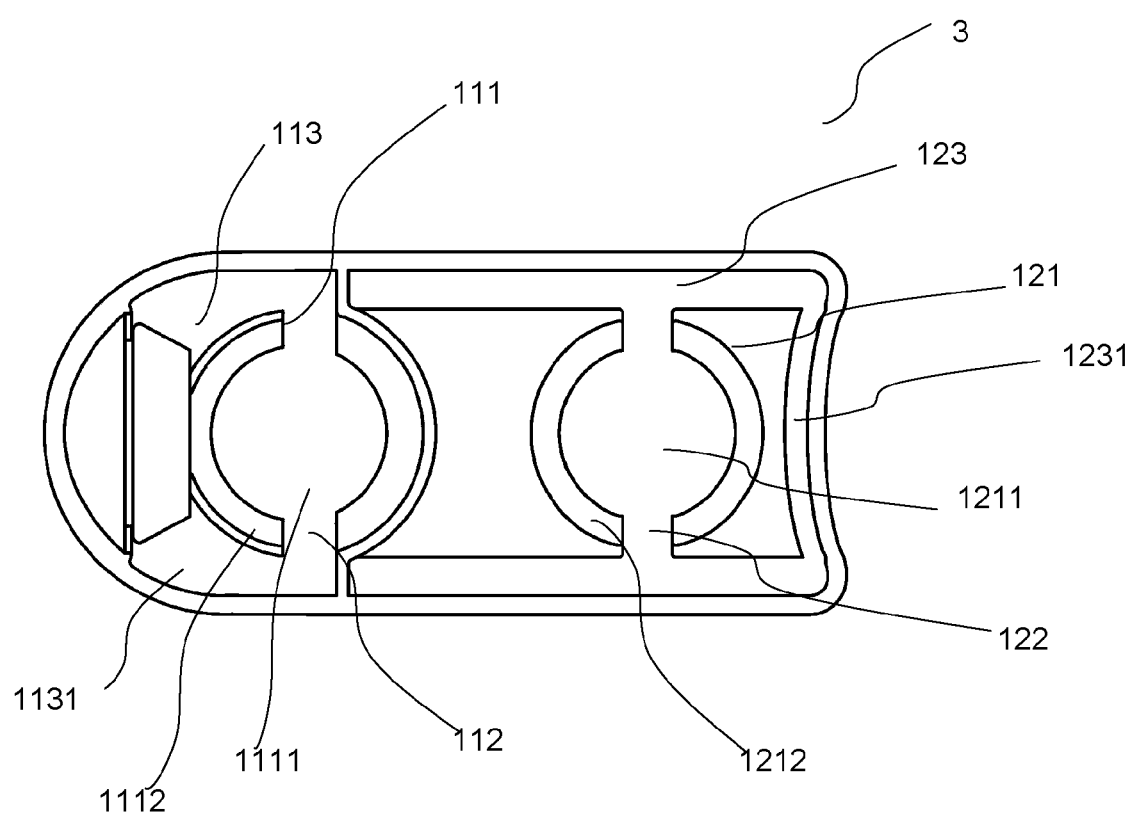
FIG. 7 illustrates a top view of the body fluid testing apparatus according to the third embodiment of the present disclosure.
Figure 8:
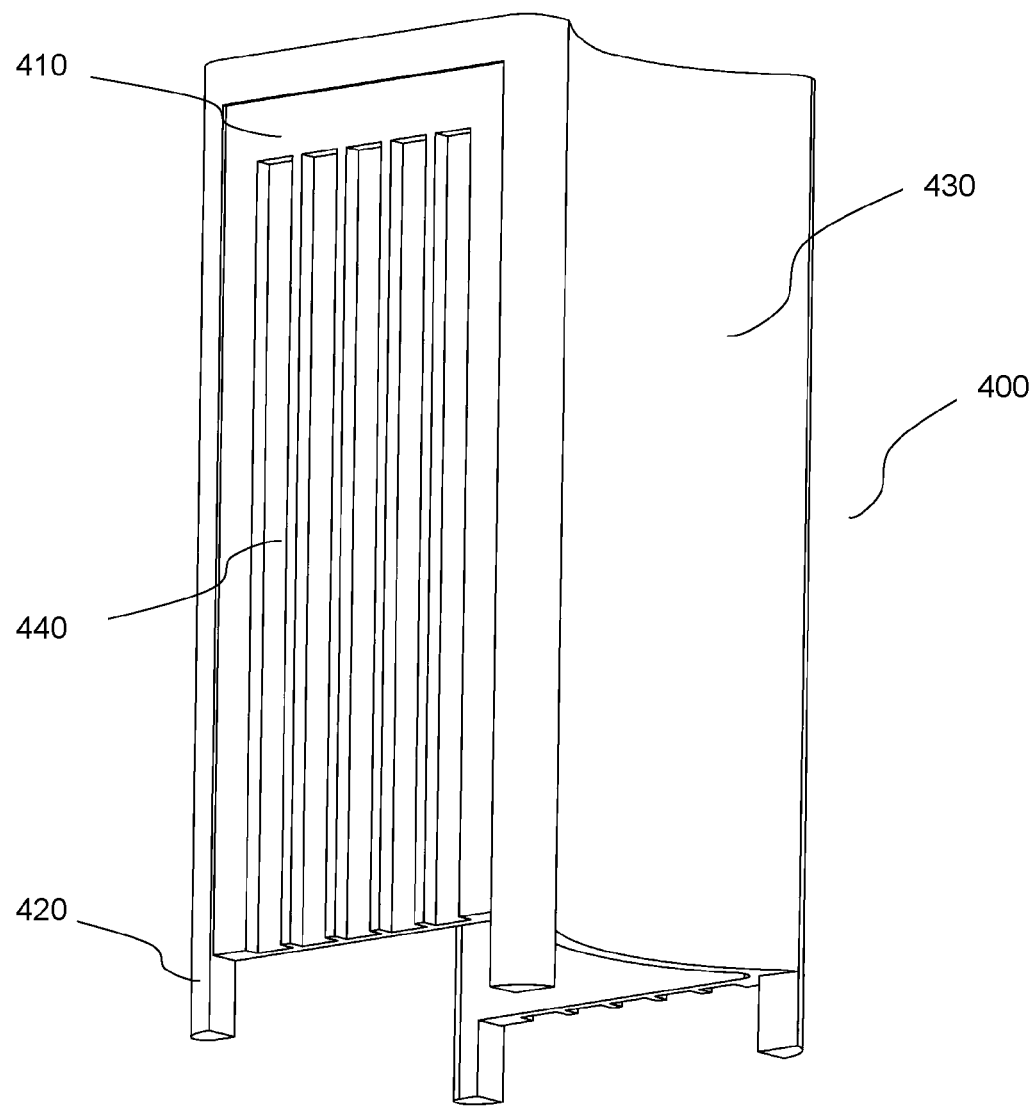
FIG. 8 illustrates a schematic view showing a testing sleeve in the body fluid testing apparatus according to the third embodiment of the present disclosure.

The body fluid testing apparatus 3 as shown in FIGS. 6-8, is substantially the same as that in the first embodiment, except for the bottom of the chamber and the slot.

In the fluid storing chamber 110 according to the present embodiment, the bottom plate 1111 of the body fluid squeezing region 111 is positioned at the same level as the bottom plate 1131 of the body fluid reservoir 113, i.e., at the same level as the lower side of the outer profile of the fluid storing chamber 110. In the testing chamber 120, the squeezing plate 1211 in the body fluid squeezing region 121 is positioned at the same level as the bottom of the slot 123. Further, the wall plate 1212 is provided with two opposing openings, which extend from the periphery of the wall plate 1212 to the squeezing plate 1211 and are communicated with the slot 123 as the body fluid flow channel 122.

Additionally, in this embodiment, the testing element 400 is a testing sleeve, as shown in FIG. 8, which further comprises a connecting plate 430. As shown in FIG. 7, the slot 123 further comprises an outside slot 1231 surrounding the outer wall of the testing chamber 120, and the lower end of the connecting plate 430 can be inserted into the outside slot 1231 of the slot 123.

Modifications may be made to the body fluid testing apparatus according to the present disclosure by those skilled in the art. For example, in shown embodiments, the body fluid flow channel is in the shape of a line or a cross, but it is not limited hereby. According to the disclosure, the cover is coupled with the body fluid collector in the manner that the external thread on the handle is engaged with the internal thread on the through-hole. However, the disclosure is not intended to be limited hereby, and the cover may be coupled with the body fluid collector in a manner of a fastener which is mounted on the handle for sealedly combining the handle to the testing chamber or the fluid storing chamber. Moreover, the opening of the fluid storing chamber can be provided on the upper surface. In addition, although the present disclosure is illustrated by example of saliva collection, the body fluid testing apparatus can also be used to test other body fluid.

Since the body fluid testing apparatus according to the present disclosure has both the testing chamber and the fluid storing chamber, it can implement accordingly both the preliminary screening and the secondary exact screening for the samples. Further, according to the present disclosure, the testing chamber and the fluid storing chamber are not communicated with each other, and thereby it can be assured that the samples to be tested are not polluted during the rescreening and not affected by the preliminary screening.

Exemplary embodiments have been specifically shown and described as above. It will be appreciated by those skilled in the art that the disclosure is not limited to the disclosed embodiments; rather, all suitable modifications and equivalent which come within the spirit and scope of the appended claims are intended to fall within the scope of the disclosure.

What is claimed is:

1. An body fluid testing apparatus with testing and storing functions, comprising: a body, a cover, at least two body fluid collectors and a testing element,
    wherein the body comprises a fluid storing chamber, a testing chamber and a partition wall, and the fluid storing chamber and the testing chamber are divided by the partition wall, such that a body fluid in the testing chamber and a body fluid in the fluid storing chamber are not in fluid communication with each other;
    wherein the cover is disposed on and covers the body and is provided with at least two through-holes, wherein the at least two body fluid collectors enter into the fluid storing chamber and the testing chamber through the at least two through-holes, respectively;
    wherein the testing element is inserted into the testing chamber and positioned against the inner wall of the testing chamber, and wherein the testing element comprises a main part having a plurality of channels for containing test strips and an inserting end extending downwardly from the main part.

2. The body fluid testing apparatus according to claim 1, wherein the body fluid collector comprises a handle, a sampling end and a connecting bar connecting the handle with the sampling end.

3. The body fluid testing apparatus according to claim 2, wherein the sampling end is made from absorbent material.

4. The body fluid testing apparatus according to claim 2, wherein a press plate is further provided on the lower end of the connecting bar, and the sampling end is connected to a bottom of the press plate.

5. The body fluid testing apparatus according to claim 1, wherein a coupling member is disposed in each of the through-holes of the cover, and the handle is provided with an adapting member matching to the coupling member.

6. The body fluid testing apparatus according to claim 5, wherein the coupling member is screw thread or fastener.

7. The body fluid testing apparatus according to claim 1, wherein the body fluid testing apparatus is a saliva testing apparatus.

8. The body fluid testing apparatus according to claim 1, wherein the fluid storing chamber comprises a body fluid squeezing region, a body fluid flow channel and a body fluid reservoir, and the body fluid squeezing region is communicated with the body fluid reservoir through the body fluid flow channel.

9. The body fluid testing apparatus according to claim 8, wherein the body fluid reservoir partly surrounds the periphery of the body fluid squeezing region, and the body fluid squeezing region comprises a squeezing plate and a wall plate extending upward from the edge of the squeezing plate.

10. The body fluid testing apparatus according to claim 9, wherein the squeezing plate in the body fluid squeezing region is positioned higher than the bottom plate of the body fluid reservoir, or positioned at the same level as the bottom plate of the body fluid reservoir.

11. The body fluid testing apparatus according to claim 9, wherein the wall plate is provided with at least one opening as the body fluid flow channel, and a lower part of the body fluid collector capable of entering into the space defined by the wall plate and the squeezing plate to avoid a horizontal displacement during being squeezed.

12. The body fluid testing apparatus according to claim 8, wherein the fluid storing chamber further comprises a partition plate, a top opening of the body fluid squeezing region is located on the partition plate, and the body fluid reservoir is located below the partition plate, the body fluid squeezing region is defined by a squeezing plate and a wall plate extending upward from the edge of the squeezing plate, and the lower part of the body fluid collector enters into the space defined by the wall plate and the squeezing plate, to avoid a horizontal displacement during being squeezed.

13. The body fluid testing apparatus according to claim 12, wherein the squeezing plate is provided with at least one opening as the body fluid flow channel.

14. The body fluid testing apparatus according to claim 1, wherein the testing chamber comprises a body fluid squeezing region, a body fluid flow channel and a slot, the slot is used to contain the inserting end of the testing element, and the body fluid flow channel connects the body fluid squeezing region with the slot.

15. The body fluid testing apparatus according to claim 14, wherein the body fluid squeezing region is defined by a squeezing plate and a wall plate extending upward from the edge of the squeezing plate, and a lower part of the body fluid collector enters into the space defined by the wall plate and the squeezing plate, to avoid a horizontal displacement during being squeezed.

16. The body fluid testing apparatus according to claim 14, wherein the body fluid flow channel is configured to be concaved from the surface of the squeezing plate and communicated with the slot, and the bottom of the slot is located at a position lower than that of the squeezing plate.

17. The body fluid testing apparatus according to claim 14, wherein the wall plate is provided with at least one opening as the body fluid flow channel, and the bottom of the slot is positioned at a same level as the squeezing plate.

18. The body fluid testing apparatus according to claim 1, wherein an opening is disposed at the side wall of the fluid storing chamber or the upper surface of the cover, which is sealed with a sealing plug provided on a covering plate of the fluid storing chamber.

19. The body fluid testing apparatus according to claim 1, wherein the front surface and the back surface of the body of the body fluid testing apparatus are parallel to each other.

* * * * *